(12) United States Patent
Kappel et al.

(10) Patent No.: US 6,972,000 B2
(45) Date of Patent: Dec. 6, 2005

(54) MANUAL/AUTO-PRIME AIR ELIMINATOR

(75) Inventors: Thomas Francis Kappel, St. Louis, MO (US); Mark Dennis Worley, Imperial, MO (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 0 days.

(21) Appl. No.: 10/646,842

(22) Filed: Aug. 25, 2003

(65) Prior Publication Data

US 2004/0039335 A1 Feb. 26, 2004

Related U.S. Application Data

(63) Continuation of application No. 09/935,690, filed on Aug. 24, 2001, now abandoned.

(51) Int. Cl.[7] .......................... A61M 1/00; A61M 5/00; A61M 5/14
(52) U.S. Cl. ...................... 604/122; 604/126; 604/129; 604/251
(58) Field of Search ................ 604/122–127, 604/251–256

(56) References Cited

U.S. PATENT DOCUMENTS

| | | | |
|---|---|---|---|
| 3,631,654 A | 1/1972 | Riely et al. | |
| 3,776,229 A * | 12/1973 | McPhee | 604/127 |
| 3,778,971 A | 12/1973 | Granger et al. | |
| 3,976,068 A * | 8/1976 | Lundquist | 604/246 |
| 4,004,587 A | 1/1977 | Jess | |
| 4,198,971 A | 4/1980 | Noiles | |
| 4,218,313 A * | 8/1980 | Aid et al. | 210/650 |
| 4,615,694 A | 10/1986 | Raines | |
| 4,900,308 A | 2/1990 | Verkaart | |
| 4,906,260 A | 3/1990 | Emheiser et al. | |
| 5,045,096 A | 9/1991 | Quang et al. | |
| 5,114,416 A * | 5/1992 | Karwoski et al. | 604/321 |
| 5,242,424 A * | 9/1993 | Chen | 604/251 |
| 5,290,237 A | 3/1994 | Verkaart | |
| 5,468,388 A | 11/1995 | Goddard et al. | |
| 5,674,200 A | 10/1997 | Ruschke et al. | |
| 6,013,061 A | 1/2000 | Kelley | |

* cited by examiner

Primary Examiner—Nicholas D. Lucchesi
Assistant Examiner—Matthew F. DeSanto
(74) Attorney, Agent, or Firm—Baker Botts L.L.P.

(57) ABSTRACT

A vent system for an infusion drip chamber is provided according to the invention. The vent system includes an automatic air eliminator communicating with an interior and an exterior of the infusion drip chamber. The automatic air eliminator is capable of automatically venting air from the infusion drip chamber in a substantially continuous manner. The vent system further includes a mechanical air eliminator communicating with the interior and the exterior of the infusion drip chamber. The manual air eliminator is capable of mechanically venting air from the infusion drip chamber at discrete time intervals.

15 Claims, 2 Drawing Sheets

MANUAL/AUTO-PRIME AIR ELIMINATOR

CROSS-REFERENCE TO RELATED APPLICATION

This application is a continuation of application Ser. No. 09/935,690, filed Aug. 24, 2001 now abandoned.

BACKGROUND OF THE INVENTION

1. Field of the Invention

The present invention relates generally to the field of intravenous fluid delivery.

2. Description of the Background Art

Intraveneous fluid delivery systems are devices used to infuse a fluid into the circulatory system of a patient. This may be done as part of medical treatment. The infusion may include infusion of fluids such as whole blood or blood components, saline solution, medications, etc. The infused fluid is therefore injected into the patient's bloodstream, where it may be circulated. A popular infusion site is in an arm of a patient.

Infusion is generally accomplished by use of a needle and tubing. The needle is inserted into a patient's blood vessel, and an infusion fluid is introduced into the tubing.

A concern during infusion is the air that may be trapped in the tubing at the start of fluid delivery. The air in the needle and tubing is displaced by the supplied fluid, and if not vented it can be transported into the patient's circulatory system as air bubbles. These bubbles may be dangerous in the patient's circulatory system. Furthermore, air bubbles may interfere with the flow of the infusion fluid. Therefore, it is imperative that all air bubbles be removed from the infusion system.

In the prior art, air bubbles are commonly removed in a manual fashion by the person administrating the infusion fluid. This comprises venting the air bubbles by opening a port or tapping the tubing to move air bubbles up into a vent opening or drip chamber.

The manual air bubble removal of the prior art has several drawbacks. It is time-consuming on the part of the person administering the infusion fluid. In addition, it is another task to be remembered and performed. Furthermore, it is subject to error or an incomplete performance.

There remains a need in the art for an improved intraveous fluid delivery.

SUMMARY OF THE INVENTION

A vent system for an infusion drip chamber is provided according to one embodiment of the invention. The vent system comprises an automatic air eliminator communicating with an interior and an exterior of the infusion drip chamber. The automatic air eliminator is capable of automatically venting air from the infusion drip chamber in a substantially continuous manner. The vent system further comprises a mechanical air eliminator communicating with the interior and the exterior of the infusion drip chamber. The manual air eliminator is capable of mechanically venting air from the infusion drip chamber at discrete time intervals.

An air venting method for an infusion drip chamber is provided according to another embodiment of the invention. The method comprises the steps of providing an automatic air eliminator capable of substantially, automatically and continuously venting the air and providing a mechanical air eliminator capable of mechanically venting the air at discrete time intervals.

The above and other features and advantages of the present invention will be further understood from the following description of the preferred embodiments thereof, taken in conjunction with the accompanying drawings.

DETAILED DESCRIPTION OF THE PREFERRED EMBODIMENTS

Figure 1:
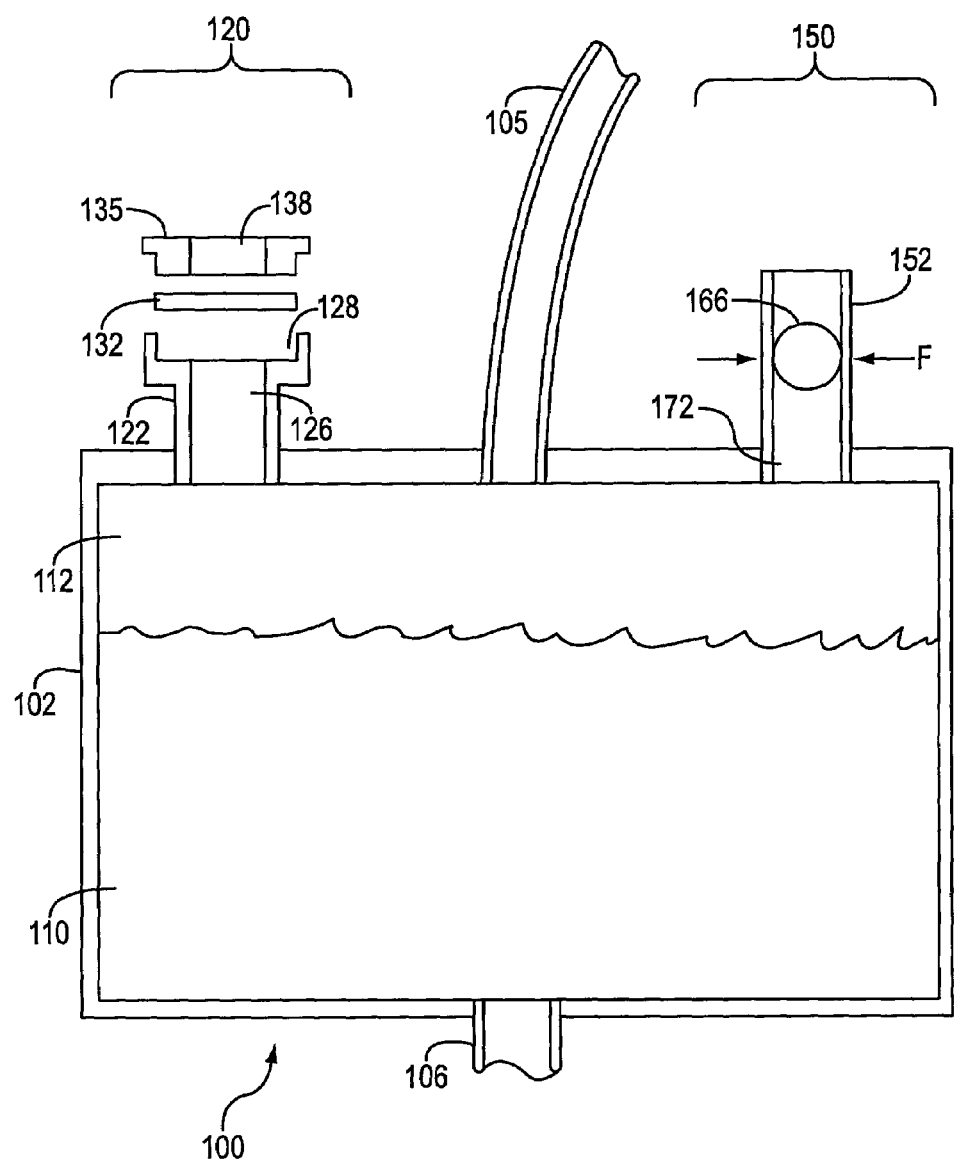
FIG. 1 is a cross-sectional diagram of a manual/auto-prime air elimination system according to one embodiment of the invention.

FIG. 1 is a cross-sectional diagram of a manual/auto-prime air elimination system 100 according to one embodiment of the invention. The manual/auto-prime air elimination system 100 includes a drip chamber 102, an inlet 105, an outlet 106, an automatic air eliminator 120, and a mechanical air eliminator 150. The drip chamber 102 may contain fluid 110 and air 112. The manual/auto-prime air elimination system 100 vents air 112 from the drip chamber 102, as it is imperative that the air 112 not travel into the outlet 106.

The automatic air eliminator 120 includes a body 122 having a body air passage 126 and a receptacle chamber 128. A hydrophobic element 132 is placed in the receptacle chamber 128. The hydrophobic element 132 may be a membrane or filter that allows air 112 to pass through but does not allow fluid 110 to pass. A cap 135 is placed on top of the hydrophobic element 132 and fits into the receptacle chamber 128. The cap 135 is retained in the receptacle chamber 128 by a friction fit or a snap fit, for example. The cap 135 further includes a cap air passage 138.

Air 112 may travel through the body air passage 126, through the hydrophobic element 132, and out the cap air passage 138. The air 112 may travel through the automatic air eliminator 120 as a result of a positive air pressure inside the drip chamber 102 due to the introduction of the fluid 110. In addition, air 112 may pass through the hydrophobic element 132 in the absence of a positive pressure.

The material of the hydrophobic element 132 may be any manner of oleophobic or hydrophobic material (referred to hereinafter only as hydrophobic for simplicity). The material of the hydrophobic element 132 may include MFLON® PTFE membrane, VERSAPOR® R membrane, SUPOR® R membrane (all available from Pall Specialty Materials), etc. The hydrophobic material allows air to vent but is repellant to fluids. The hydrophobic material allows air to pass until the material becomes wetted. Wetting is a saturation of the pores of the hydrophobic material. If wetting occurs, further air cannot pass through the material.

The mechanical air eliminator 150 in the embodiment shown includes a deformable conduit 152 that fits into a port 172 in the drip chamber 102. A deformable ball 166 is positioned in the conduit 152 and normally substantially blocks and seals the conduit 152.

When the conduit 152 and the ball 166 are manually deformed or squeezed by a force F, air 112 is allowed to pass around the ball 166 and through the conduit 152. When the deforming force F is removed, the ball 166 resumes its normal shape and the mechanical venting ceases.

The automatic air eliminator 120 and the mechanical air eliminator 150 may be attached to any three-port drip chamber, as shown. Alternatively, the mechanical air eliminator 150 and the automatic air eliminator 120 may be combined into a single device (not shown) sharing a common conduit and fitting into an available port of a two-port drip chamber.

In operation, air 112 may substantially, automatically and continuously vent through the automatic air eliminator 120 by passing through the hydrophobic element 132. The automatic air eliminator 120 therefore substantially, automatically and continuously vents air, and does so without need of human intervention. In addition, the mechanical air eliminator 150 may operate at discrete time intervals to vent air. The mechanical air eliminator 150 or 250 may mechanically operate (open) in response to a predetermined positive air pressure in the drip chamber 102 (see FIG. 2 and accompanying text), or may be manually operated by a technician. The manual mechanical air eliminator 150 may be manually operated at any time, although it likely will be used when the automatic air eliminator 120 is not adequately venting air.

Figure 2:
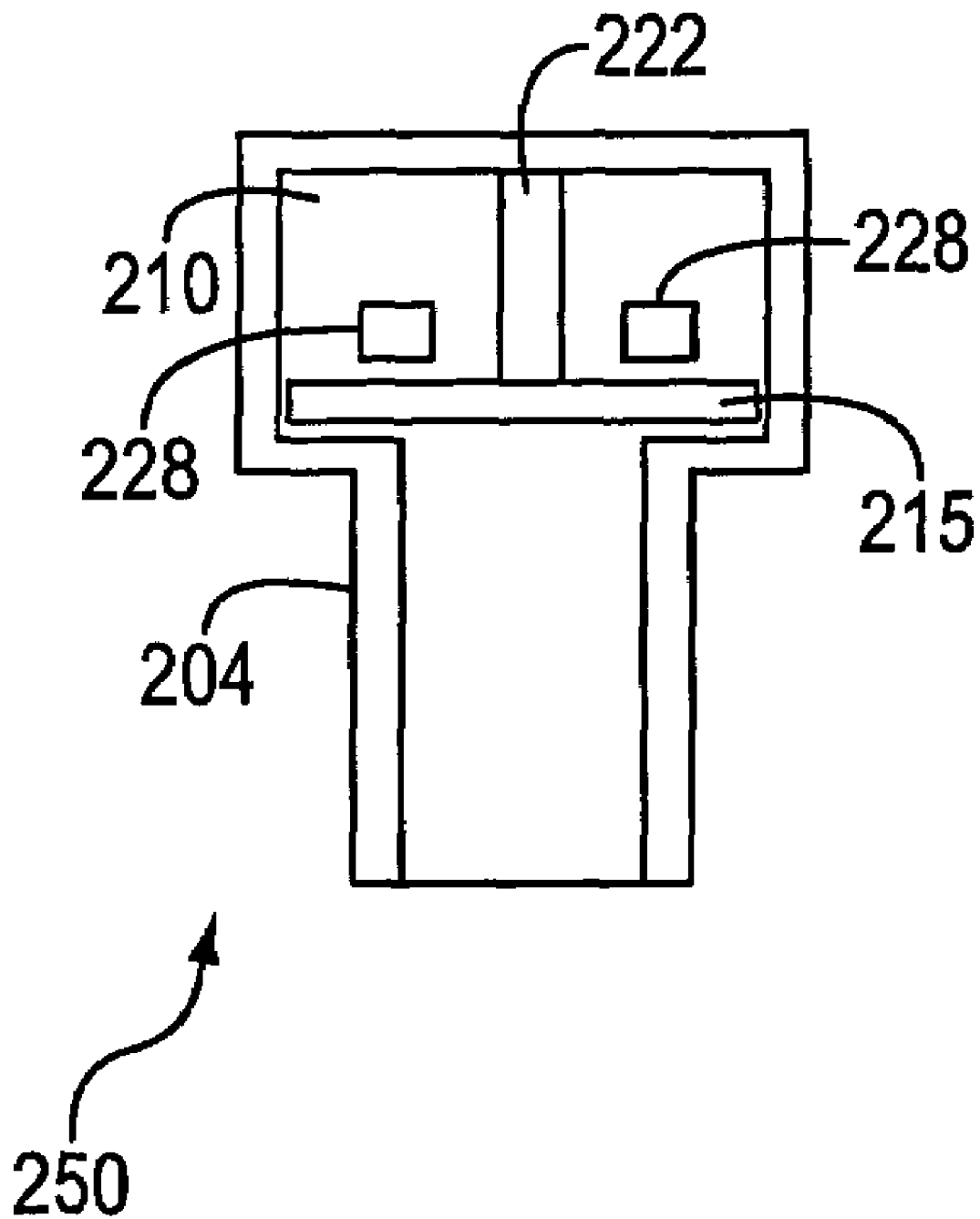
FIG. 2 is a cross-sectional diagram of a mechanical air eliminator according to another embodiment of the invention.

FIG. 2 is a cross-sectional diagram of a mechanical air eliminator 250 according to another embodiment of the invention. The mechanical air eliminator 250 may be used in place of the previously shown and discussed manual mechanical air eliminator 150.

The mechanical air eliminator 250 includes a conduit 204, a plunger 215, a plunger chamber 210, a biasing device 222, and at least one vent opening 228.

The conduit 204 may fit into a port in the drip chamber 102, as in the manual mechanical air eliminator 150. The conduit 204 communicates air 112 from the drip chamber 102 into the plunger chamber 210. The plunger 215 is normally held in a position blocking the conduit 204 by the biasing device 222. The biasing device 222 may be any manner of spring, diaphragm, etc., that provides a biasing force to hold the plunger 215 in a normally closed position in an absence of a positive air pressure inside the drip chamber 102. The biasing device 222 may be selected so that the plunger opens in response to a predetermined positive air pressure in the drip chamber 102. Therefore, the plunger 215 may mechanically open at discrete time intervals in order to vent air. When the plunger 215 is displaced by a positive air pressure, the at least one vent opening 228 may be placed in communication with the conduit 204, allowing air venting for the drip chamber 102.

The combination of the automatic air eliminator 120 and the mechanical air eliminator 150 or 250 enables a complete air venting of the drip chamber 102. In addition, the combination allows the air 112 to be automatically vented, and with the manual mechanical air eliminator 150 or 250 providing additional venting if the air 112 is not being adequately vented by the automatic air eliminator 120. Furthermore, the mechanical air eliminator 150 or 250 may be used if the hydrophobic element 132 of the automatic air eliminator 120 becomes wetted or clogged and no longer allows air to pass. Moreover, the mechanical air eliminator 150 or 250 may be used in conjunction with the automatic air eliminator 120 in order to increase the venting rate. Therefore, the air 112 may be removed as desired, preventing air from passing through the outlet 106 and enabling a fluid prime of the outlet 106.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A vent system for an infusion drip chamber, comprising:
   an automatic air eliminator communicating with an interior and an exterior of said infusion drip chamber, a passageway positioned between said interior and said exterior, said interior for containing fluids, said automatic air eliminator positioned between said interior and said exterior, said automatic air eliminator being capable of automatically venting air from said infusion drip chamber in a substantially continuous manner, said automatic air eliminator positioned in said passageway for preventing other fluids from passing from said interior to said exterior;
   a mechanical air eliminator communicating with said interior and said exterior of said infusion drip chamber and capable of mechanically venting air from said infusion drip chamber at discrete time intervals, said mechanical air eliminator comprising:
   a conduit capable of fitting in a port of said infusion drip chamber;
   a plunger chamber formed in said conduit;
   a plunger movable in said plunger chamber;
   a biasing device operative to maintain said plunger in a normally closed position; and
   at least one vent opening in said plunger chamber and communicating with said exterior of said infusion drip chamber, with said at least one vent opening being spaced apart from said plunger when said plunger is in said normally closed position;
   wherein said plunger is capable of being displaced by a positive air pressure in said drip chamber until said at least one vent opening communicates with said interior of said infusion drip chamber and vents said infusion drip chamber.

2. The system of claim 1, with said automatic air eliminator further comprising:
   a body including a body air passage, said body air passage communicates with said interior of said infusion drip chamber;
   a hydrophobic element capable of allowing air to pass through and capable of blocking fluid;
   a receptacle chamber capable of receiving said hydrophobic element; and
   a cap including a cap air passage and capable of fitting in said receptacle chamber and retaining said hydrophobic element;
   wherein said cap air passage communicates with said exterior of said infusion drip chamber and is substantially aligned with said body air passage when said cap is in position at least partially in said receptacle chamber and wherein vented air must pass through said hydrophobic element.

3. The system of claim 2, wherein said cap is retained in said receptacle chamber by a friction fit.

4. The system of claim 2, wherein said cap is retained in said receptacle chamber by a snap fit.

5. The system of claim 2, wherein said cap air passage is substantially coaxial with said body air passage when said cap is in position at least partially in said receptacle chamber.

6. The system of claim 1, wherein said mechanical air eliminator and said automatic air eliminator are capable of simultaneously eliminating air from said infusion drip chamber.

7. The system of claim 1, wherein said mechanical venting occurs independently of said automatic venting.

8. The system of claim 1, wherein said mechanical venting occurs after said automatic venting.

9. The system of claim 1, wherein said mechanical air eliminator and said automatic air eliminator are capable of being used in combination to increase an air venting rate.

10. The system of claim 1, wherein said automatic air eliminator includes a hydrophobic element and wherein said mechanical air eliminator is capable of eliminating air from said infusion drip chamber even when said hydrophobic element of said automatic air eliminator is wetted.

11. An air venting method for an infusion drip chamber, comprising:

provinding an automatic air eliminator communicating with an interior and an exterior of said infusion drip chamber, a passageway positioned between said interior and said exterior, said interior for containing fluids, said automatic air eliminator positioned between said interior and said exterior, said automatic air eliminator being capable of substantially, automatically and continuously venting said air, said automatic air eliminator positioned in said passageway for preventing other fluids from passing from said interior to said exterior; and providing a mechanical air eliminator capable of mechanically venting said air at discrete time intervals by:

fitting a conduit in a port of said infusion drip chamber;

forming a plunger chamber in said conduit;

moving a plunger in said plunger chamber;

biasing said plunger in a normally closed position; and opening a vent in said plunger chamber and communicating with said exterior of said infusion drip chamber, with said at least one vent opening being spaced apart from said plunger when said plunger is in said normally closed position; and displacing said plunger by a positive air pressure in said drip chamber until said at least one vent opening communicates with said interior of said infusion drip chamber and vents said infusion drip chamber.

12. The method of claim 11, further comprising manually manipulating said mechanical air eliminator to vent said air when a hydrophobic element of said automatic air eliminator is wetted.

13. The method of claim 11, further comprising mechanically venting after said automatic venting.

14. The method of claim 11, further comprising mechanically venting simultaneously with said automatic venting.

15. The method of claim 11, further comprising mechanically venting independently of said automatic venting.

* * * * *